United States Patent
Bienewald et al.

(10) Patent No.: US 11,401,227 B2
(45) Date of Patent: Aug. 2, 2022

(54) PROCESS TO PRODUCE A MONO VINYL ETHER

(71) Applicant: BASF SE, Ludwigshafen am Rhein (DE)

(72) Inventors: Frank Bienewald, Ludwigshafen (DE); Martin Voelkert, Ludwigshafen (DE); Rolf Pinkos, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 17/271,419

(22) PCT Filed: Aug. 19, 2019

(86) PCT No.: PCT/EP2019/072078
§ 371 (c)(1),
(2) Date: Feb. 25, 2021

(87) PCT Pub. No.: WO2020/043518
PCT Pub. Date: Mar. 5, 2020

(65) Prior Publication Data
US 2021/0340090 A1    Nov. 4, 2021

(30) Foreign Application Priority Data

Aug. 30, 2018 (EP) ..................... 18191738

(51) Int. Cl.
*C07C 41/08* (2006.01)
*C07C 41/44* (2006.01)

(52) U.S. Cl.
CPC .............. *C07C 41/08* (2013.01); *C07C 41/44* (2013.01); *C07C 2601/14* (2017.05)

(58) Field of Classification Search
CPC ...... C07C 41/08; C07C 41/44; C07C 2601/14
See application file for complete search history.

(56) References Cited

U.S. PATENT DOCUMENTS

| | | | |
|---|---|---|---|
| 6,794,546 B2 | 9/2004 | Pinkos et al. | |
| 7,670,464 B2 | 3/2010 | Klass et al. | |
| 2010/0249465 A1* | 9/2010 | Tenjimbayashi | C07C 43/303 |
| | | | 568/689 |

FOREIGN PATENT DOCUMENTS

| | | |
|---|---|---|
| JP | H10-158208 A | 6/1998 |
| JP | H10-218823 A | 8/1998 |
| WO | WO-2018/036848 A2 | 3/2018 |

OTHER PUBLICATIONS

International Search Report for PCT Patent Application No. PCT/EP2019/072078,dated Nov. 15, 2019, 3 pages.

* cited by examiner

*Primary Examiner* — Rosalynd A Keys
(74) *Attorney, Agent, or Firm* — Grüneberg and Myers PLLC

(57) ABSTRACT

A process produces a mono vinyl ether, R—O—CH=CH$_2$. R represents an organic group with at least three carbon atoms. The process involves reacting a mono hydroxy compound. R—OH, with acetylene in presence of a catalyst to get a product mixture containing the mono vinyl ether, unconverted mono hydroxy compound, and the catalyst. To the product mixture, an ester is added that contains at least one ester group, X—O$_2$C—. X is a hydrocarbon group containing less carbon atoms than R. The remaining mono hydroxy compound R—OH is reacted with the ester in the presence of the catalyst to get a transesterification product containing at least one ester group, R—O$_2$C—, and an alcohol, X—OH. The mono vinyl ether is isolated from the product mixture obtained after the ester addition, optionally followed by purification of the mono vinyl ether by distillation.

10 Claims, No Drawings

PROCESS TO PRODUCE A MONO VINYL ETHER

CROSS-REFERENCE TO RELATED APPLICATIONS

This application is the National Stage entry under § 371 of International Application No. PCT/EP2019/072078, filed on Aug. 19, 2019, and which claims the benefit of European Application No. 18191738.6, filed on Aug. 30, 2018. The content of each of these applications is hereby incorporated by reference in its entirety.

BACKGROUND OF THE INVENTION

Field of the Invention

The present invention relates to a process to produce a mono vinyl ether of formula I $$R-O-CH=CH_2$$

wherein R represents an organic group with at least three carbon atoms
comprising
a) reacting a mono hydroxy compound of formula II $$R-OH$$

wherein R has the above meaning
with acetylene in presence of a catalyst to get a product mixture comprising the mono vinyl ether, unconverted mono hydroxy compound and the catalyst
b) adding an ester comprising at least one ester group of formula III $$X-O_2C-$$

wherein X is a hydrocarbon group comprising less carbon atoms than R
to the product mixture obtained in process step a) and reacting the remaining mono hydroxy compound R—OH with the ester in the presence of the catalyst to get a transesterification product comprising at least one ester group of formula IV $$R-O_2C-$$

and an alcohol of formula V $$X-OH$$

wherein R and X have the above meaning
and
c) isolating the mono vinyl ether from the product mixture obtained after process step b), optionally followed by purification of the mono vinyl ether by distillation.

Description of Related Art

A well-known process for the synthesis of a vinyl ether is the Reppe process. According to the Reppe process a vinyl ether is obtained by reacting an alcohol with acetylene in presence of a basic catalyst. Usually, the catalyst is the sodium or a potassium alcoholate. The catalyst is easily obtained by adding sodium or potassium hydroxide to the alcohol in an amount that 0.5 to 5% by weight of the alcohol are turned into the corresponding alcoholate. The obtained mixture of alcohol and the corresponding sodium or potassium alcoholate is then reacted with acetylene. Such a process is described, for example, in U.S. Pat. No. 6,794,546 or WO 2018/036848.

At high conversions of the alcohol, the viscosity increases significantly, gel formation might occur and formation of polymer and/or other residual products is often observed. Furthermore, high conversions require a long residence time in the reactor, which is uneconomically.

Therefore, the reaction may be terminated at lower conversions of the alcohol, thus obtaining a product mixture comprising the vinyl ether and major amounts of the unconverted alcohol. The vinyl ether needs to be separated from the mixture. A separation by distillation is known from U.S. Pat. No. 7,670,464. As stated in the US patent, a distillation cannot be performed easily, due to azeotrope formation. The distillation process suggested in the US patent is a two-step distillation in separated columns with a recycling of the azeotrope from the second into the first column.

SUMMARY OF THE INVENTION

It was an object of this invention to provide a process for the production of vinyl ethers comprising an easy and economic separation of vinyl ether and unconverted alcohol.

Hence, the process defined above has been found.

DETAILED DESCRIPTION OF THE INVENTION

To the mono vinyl ether of formula I

R in formula I represents an organic group with at least three carbon atoms.

Preferably, R in formula I represents an organic group with 3 to 20 carbon atoms, more preferably 3 to 10 carbon atoms. R does not comprise hydroxy groups. The organic group may comprise other atoms than carbon and hydrogen atoms in form of functional groups that are not reactive with acetylene. For example, the organic group may comprise oxygen atoms in form of ether or carbonyl groups.

More preferably, R in formula I represents a hydrocarbon group and does not comprise other atoms than carbon or hydrogen atoms.

Most preferably, R in formula I represents a non-aromatic hydrocarbon group with 3 to 10 carbon atoms. Such hydrocarbon group may be an alkyl group or a cycloalkyl group.

In a particularly preferred embodiment of the invention, R is a cyclohexyl group.

To Process Step a)

Starting materials of process step a) are acetylene, the mono hydroxy compound of formula II and the catalyst.

The mono hydroxy compound of formula II corresponds to the desired mono vinyl ether of formula I and R in formula II has the same meaning as in formula I.

Hence, the mono hydroxy compound of formula II is most preferably a hydrocarbon with 3 to 10 carbon atoms substituted by one hydroxy group, notably a C3 to C10 alkanol or cyclohexanol. In a particularly preferred embodiment, the mono hydroxy compound is cyclohexanol.

The catalyst is preferably a metal alcoholate of formula VI $$RO^-M^+$$

wherein R has the above meaning and $M^+$ represents a metal cation.

Preferably, $M^+$ is an alkali cation such as the cation of sodium or potassium, most preferably of potassium.

Preferably, the metal alcoholate $RO^-M^+$ is the metal alcoholate of the mono hydroxy compound to be reacted with acetylene.

The metal alcoholate may be prepared separately and may then be added to the reaction mixture of step a).

In a preferred embodiment, the metal alcoholate is prepared by adding a metal hydroxide, preferably an alkali metal hydroxide, most preferably sodium or potassium hydroxide to the mono hydroxy compound of formula II. Preferably, the alkali metal hydroxide is used in the form of an aqueous solution.

The reaction of the mono hydroxy compound of formula II with the alkali metal hydroxide is preferably performed at temperatures of from 50 to 250° C. and from 1 mbar to 1 bar.

Preferably, the catalyst is used in an amount of 0.1 to 10 parts by weight, more preferably in an amount of 0.5 to 7 parts by weight per 100 parts by weight of the mono hydroxy compound. In the above process for the preparation of the metal alcoholate the amount of alkali metal hydroxide is chosen accordingly.

The vinylation of the mono hydroxy compound with acetylene in presence of the catalyst is preferably performed at 120 to 220° C.

The reaction may be performed under reduced or elevated pressure, for example at a pressure of 0.1 to 25 bars, notably at a pressure of 1 to 20 bars. The pressure may be the pressure of acetylene itself or of mixtures of acetylene with an inert gas.

The reaction in the first step is terminated before the total amount of the mono hydroxy compound has reacted. Preferably, the reaction is terminated when 70 to 99%, more preferably 90 to 99% of the mono hydroxy compound have been consumed. Consumption of the mono hydroxy compound may be determined by gas chromatography.

The reaction may be terminated by decreasing the temperature and/or releasing the pressure and/or by stopping the acetylene feed.

The product mixture obtained in step a) comprises the mono vinyl ether of formula I, unconverted mono hydroxy compound of formula II and catalyst.

Preferably, the product mixture obtained in step a) comprises
55 to 98.9% by weight of the mono vinyl ether of formula I
1 to 35% by weight of the mono hydroxy compound of formula II and
0.1 to 10% by weight of the catalyst
based on 100% by weight of the product mixture.

More preferably, the product mixture obtained in step a) comprises
85 to 97% by weight of the mono vinyl ether of formula I
2 to 10% by weight of the mono hydroxy compound of formula II and
1 to 5% by weight of the catalyst
based on 100% by weight of the product mixture.

The reaction of process step a) may be performed in a single reactor or in several successive reactors, for example a reactor battery. Suitable reactors include stirred tank reactors, batteries of stirred tank reactors, flow tubes, bubble columns and loop reactors. The acetylene is preferably introduced through the stirrer (in case of stirred tank reactors) or through nozzles.

Process step a) may be performed as batch process, semi-continuous process or continuous process. In a batch process all starting materials are added to the reactor before the reaction is started, in a semi-continuous process at least one of the starting materials is fed continuously during the reaction and in a continuous process all starting materials are fed continuously to the reactor and all products are withdrawn continuously from the reactor.

In a preferred embodiment, process step a) is performed semi-continuously by adding the whole amount of alcohol to the reactor and then steadily feeding acetylene to the reactor until the desired conversion of the alcohol is achieved.

To Process Step b)

Preferably, the product mixture obtained in step a) is used in step b) without any prior work-up or removal of compounds.

In process step b) an ester comprising at least one ester group of formula III

X—O$_2$C— wherein X is a hydrocarbon group comprising less carbon atoms than R, is added to the product mixture obtained in process step a).

Preferably, X in formula III is a methyl or ethyl group.
More preferably, X in formula III is a methyl group.
Preferably, the ester comprises one to three ester groups of formula III.
More preferably, the ester comprises one or two ester groups of formula III.
Preferably, the ester is a compound with a molecular weight of 100 to 500 g/mol, notably of 150 to 400 g/mol.

In a particularly preferred embodiment of the invention, the ester added in step b) is an ester of formula VII

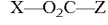

X—O$_2$C—Z wherein X has the above meaning and Z represents a hydrocarbon group with 6 to 20 carbon atoms
or of formula VIII

X—O$_2$C—CO$_2$—X wherein X has the above meaning.

Preferably, Z in formula VII represents a hydrocarbon group with 12 to 20, notably 14 to 20 carbon atoms. Examples of esters of formula III are methyl esters of fatty acids, such as the methyl ester of a C16 or C18 fatty acids or mixtures thereof. Such methyl esters of fatty acids are known, for example, as Biodiesel.

A preferred ester of formula VIII is the dimethyl ester of oxalic acid (H$_3$C—O$_2$C—CO$_2$—CH$_3$).

Preferably, the ester is added in an amount of 80 to 300, notably of 100 to 200 mols per 100 mols of the unconverted mono hydroxy compound of formula II in the product mixture obtained in step a).

The reaction in step b) is a transesterification resulting in a new ester referred to as transesterification product. The transesterification product comprises at least one ester group of formula IV

R—O$_2$C—

In addition, from the transesterification results an alcohol of formula V

X—OH wherein R and X have the above meaning and preferred meanings.

In case of the preferred esters of formula VII, the obtained transesterification product is R—O$_2$C—Z and the alcohol is X—OH, which is preferably ethanol or methanol, notably methanol.

In case of the preferred esters of formula VIII, the obtained transesterification product is R—O$_2$C—CO$_2$—R or R—O$_2$C—CO$_2$—X or mixtures thereof and the alcohol is X—OH, which is preferably ethanol or methanol, notably methanol.

The transesterification in step b) is preferably performed at a temperature of 20 to 100° C., notably at 50 to 90° C.

Preferably, the alcohol formed, notably methanol, is removed during the reaction. To facilitate the removal of the alcohol, the reaction mixture may be stripped with an inert gas, for example nitrogen.

The catalyst used in step a) serves also as catalyst for the transesterification in step b). No further catalyst is required in step b) and, preferably, no further catalyst is added.

The reaction of process step b) may also be performed in a single reactor or in several successive reactors, for example a reactor battery. Suitable reactors include stirred tank reactors, batteries of stirred tank reactors, flow tubes, bubble columns and loop reactors.

Process step b) may be performed as batch process, semi-continuous process or continuous process.

In a preferred embodiment, process step b) is performed as batch process.

To Process Step c)

In process step c) the mono vinyl ether is isolated from the product mixture obtained after process step b), optionally followed by purification of the mono vinyl ether by distillation.

The product mixture obtained at the end of step b) comprises the mono vinyl ether of formula I, the transesterification product comprising at least one ester group of formula IV, optionally some unconverted mono hydroxy compound of formula II and optionally some unconverted ester comprising ester groups of formula III. The alcohol X—OH is preferably already totally removed during the reaction in step b).

Preferably, the mono vinyl ether is separated from the product mixture by distillation. The transesterification product and the unconverted ester have a significantly higher boiling point than the mono vinyl ether, so that the mono vinyl ether can be easily separated from the product mixture by any method of distillation, for example by thin film distillation in a thin film evaporator. The obtained mono vinyl ether may still comprise minor amounts of unconverted mono hydroxy compound which can be further reduced by fractional distillation, if desired.

Process steps b) and c) may be combined and performed in one reactor, respectively column. Such combination of process steps b) and c) would preferably be a reactive distillation wherein the transesterification is performed in a column and the vinylether is simultaneously withdrawn from the column by distillation.

The removal of the vinyl ether in step c) and the further purification of the vinyl ether as well as combination of steps b) and c) by reactive distillation may be performed as batch process or continuous process. In a preferred embodiment, process step c) is performed as batch process.

The mono vinyl ether finally obtained comprises preferably less than 1% by weight, more preferably less than 0.7% by weight and most preferably less than 0.5% by weight of unconverted alcohol.

The process of this invention is an easy and economic process to produce mono vinyl ethers. The mono vinyl ethers are obtained in high yields. Complex distillation procedures for the separation of the mono vinyl ether from the product mixture as described, for example, in U.S. Pat. No. 7,670,464 are avoided.

EXAMPLE

A crude product mixture containing 90% by weight cyclohexyl vinyl ether (CHVE), 6% by weight of cyclohexanol (CH) and 4% by weight of the potassium salt of CH was obtained by vinylating CH with acetylene in the presence of KOH.

To 800 g of this crude product mixture 300 g of Biodiesel, which is the methyl ester of C16 to 018 fatty acids, was added over 3 h at 75° C., while constantly bubbling 20 l/h nitrogen through the solution to remove the formed methanol. After additional stirring and nitrogen stripping of 2 h, 1025 g of a product mixture comprising 86% by weight CHVE, 1% by weight of CH and 13% by weight of high boiling products which includes the transesterification product (ester of CH and C16 to C18 fatty acids).

The composition of the product mixture has been determined by gas chromatography (GC) by measuring the area percentages of the corresponding peaks.

887 g of this product mixture were distilled in a 0.046 m² thin film evaporator at 2.5 mbar and 105-125° C. 620 g of a lightly yellow product was withdrawn from the top of the film evaporator as distillate. The distillate comprised 98.2% CHVE and 0.3% CH. Again, the composition of the distillate has been determined by GC as described above.

High boiling compounds were removed from the bottom of the thin film evaporator.

Thereafter a fractional distillation of the obtained mixture of CHVE and CH was performed in a 30 cm packed column at 100 mbar and 110° C. bath temperature, yielding 575 g of a colorless liquid comprising 99.5% by weight of CHVE and 0.4% by weight of CH.

The invention claimed is:

1. A process to produce a mono vinyl ether of formula I

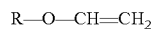

R—O—CH=CH$_2$ wherein R represents an organic group with at least three carbon atoms, the process comprising:

a) reacting a mono hydroxy compound of formula II

R—OH wherein R has the above meaning, with acetylene in presence of a catalyst to get a product mixture comprising the mono vinyl ether, unconverted mono hydroxy compound, and the catalyst;

b) adding an ester comprising at least one ester group of formula III

X—O$_2$C— wherein X is a hydrocarbon group comprising less carbon atoms than R, to the product mixture obtained in a) and reacting the remaining mono hydroxy compound R—OH with the ester in the presence of the catalyst to get a transesterification product comprising at least one ester group of formula IV

R—O$_2$C— and an alcohol of formula V

X—OH wherein R and X have the above meaning; and c) isolating the mono vinyl ether from a product mixture obtained after b), optionally followed by purification of the mono vinyl ether by distillation.

2. The process according to claim 1, wherein R in formula I represents a non-aromatic hydrocarbon group with 3 to 10 carbon atoms.

3. The process according to claim 1, wherein R in formula I is a cyclohexyl group.

4. The process according to claim 1, wherein the catalyst is an alcoholate of formula VI

RO⁻M⁺ wherein R represents an organic group with at least three carbon atoms and M⁺ represents a metal cation.

5. The process according to claim 1, wherein the catalyst is used in an amount of 0.1 to 10 parts by weight per 100 parts by weight of the mono hydroxy compound.

6. The process according to claim 1, wherein the product mixture obtained in a) comprises
- 55 to 98.9% by weight of the mono vinyl ether of formula I,
- 1 to 35% by weight of the mono hydroxy compound of formula II, and
- 0.1 to 10% by weight of the catalyst, based on 100% by weight of the product mixture.

7. The process according to claim 1, wherein X its formula III represents a methyl or ethyl group.

8. The process according to claim 1, wherein the ester added in b) comprises one or two ester groups of formula III.

9. The process according to claim 1, wherein the ester added in b) is an ester of formula VII $$X\text{---}O_2C\text{---}Z$$

wherein X is a hydrocarbon group comprising less carbon atoms than R and

Z represents a hydrocarbon group with 6 to 20 carbon atoms, or of formula VIII $$X\text{---}O_2C\text{---}CO_2\text{---}X$$

wherein X is a hydrocarbon group comprising less carbon atoms than R.

10. The process according to claim 1, wherein the ester is added in b) in an amount of 100 to 200 parts by weight per 100 parts by weight of the unconverted mono hydroxy compound of formula II in the product mixture.

* * * * *